US012608651B2

(12) United States Patent
Neumann

(10) Patent No.: US 12,608,651 B2
(45) Date of Patent: Apr. 21, 2026

(54) METHOD AND SYSTEM FOR GENERATING AN ALIMENTARY ELEMENT PREDICTION MACHINE-LEARNING MODEL

(71) Applicant: KPN INNOVATIONS, LLC.,
Lakewood, CO (US)

(72) Inventor: Kenneth Neumann, Lakewood, CO
(US)

(73) Assignee: KPN INNOVATIONS, LLC,
Lakewood, CO (US)

( * ) Notice: Subject to any disclaimer, the term of this
patent is extended or adjusted under 35
U.S.C. 154(b) by 0 days.

(21) Appl. No.: 18/113,922

(22) Filed: Feb. 24, 2023

(65) Prior Publication Data

US 2023/0214721 A1 Jul. 6, 2023

Related U.S. Application Data

(63) Continuation of application No. 17/088,146, filed on
Nov. 3, 2020, now Pat. No. 11,599,831.

(51) Int. Cl.
G06N 20/00 (2019.01)
G06F 3/0482 (2013.01)
G16H 20/60 (2018.01)

(52) U.S. Cl.
CPC ........... G06N 20/00 (2019.01); G06F 3/0482
(2013.01); G16H 20/60 (2018.01)

(58) Field of Classification Search
CPC ....... G06N 20/00; G16H 20/60; G06F 3/0482
See application file for complete search history.

(56) References Cited

U.S. PATENT DOCUMENTS

| 2002/0165839 | A1* | 11/2002 | Taylor | ................... | G06F 18/211 |
| | | | | | 706/20 |
| 2018/0157984 | A1 | 6/2018 | O'Herlihy et al. | | |
| 2018/0272066 | A1* | 9/2018 | McMahon | ............. | G16H 20/60 |
| 2019/0290172 | A1* | 9/2019 | Hadad | .................. | A61B 5/0022 |
| 2023/0157320 | A1* | 5/2023 | Roche | ................ | G09B 19/0092 |
| | | | | | 119/174 |

OTHER PUBLICATIONS

Sokołowska, Beata, Adam Jóźwik, and Mieczysław Pokorski. "A fuzzy-classifier system to distinguish respiratory patterns evolving after diaphragm paralysis in the cat." The Japanese journal of physiology 53, No. 4 (2003): 301-307. (Year: 2003).*

(Continued)

*Primary Examiner* — Casey R. Garner
(74) *Attorney, Agent, or Firm* — Caldwell LLC

(57) ABSTRACT

A system for a generating an alimentary element prediction machine-learning model, the system comprising a computing device configured to provide, to a user, a plurality of compatible alimentary elements as a function of user biochemistry, receive training data relating a plurality of temporally preceding alimentary elements as a function of the plurality of compatible alimentary elements presented to a user, train, using a machine-learning process, a computer model as a function of the user-selection training data to predict user-selectable alimentary elements, generate an alimentary profile as a function of the computer model, receive a user input for an alimentary element, and present, as a function of the user input, the alimentary element as a function of the alimentary profile.

18 Claims, 7 Drawing Sheets

(56) References Cited

OTHER PUBLICATIONS

Goldstein, Stephanie P., Fengqing Zhang, John G. Thomas, Meghan L. Butryn, James D. Herbert, and Evan M. Forman. "Application of machine learning to predict dietary lapses during weight loss." Journal of diabetes science and technology 12, No. 5 (2018): 1045-1052. (Year: 2018).*

* cited by examiner

METHOD AND SYSTEM FOR GENERATING AN ALIMENTARY ELEMENT PREDICTION MACHINE-LEARNING MODEL

CROSS-REFERENCE TO RELATED APPLICATIONS

This application is a continuation-in-part of Non-provisional application Ser. No. 17/088,146 filed on Nov. 3, 2020 and entitled "A METHOD AND SYSTEM FOR GENERATING AN ALIMENTARY ELEMENT PREDICTION MACHINE-LEARNING MODEL," the entirety of which is incorporated herein by reference.

FIELD OF THE INVENTION

The present invention generally relates to the field of machine-learning. In particular, the present invention is directed to methods and systems for generating an alimentary element prediction machine-learning model.

BACKGROUND

Updating presentation of alimentary elements aimed at improving user physiology is typically based on returning solutions that were determined through convoluted pipelines. Generating newer options as a function of user feedback, such as taste, preference, and previous selection are difficult to achieve while being mindful of user physiology.

SUMMARY OF THE DISCLOSURE

In an aspect, a system for a identifying an insufficient alimentary element, the system including a computing device, wherein the computing device is designed and configured to receive a plurality of preceding alimentary elements; generate an adherence score based on the plurality of preceding alimentary elements, wherein the adherence score is related to adherence of a alimentary element program; identify, as a function of the adherence score, an insufficiency of an alimentary element of the of the plurality of preceding alimentary elements; and generate an alimentary instruction set of an alimentary element program, wherein the alimentary instruction set addresses the insufficiency.

In another aspect, a method receiving, by at least a computing device, a plurality of preceding alimentary elements; generating, by the at least computing device, an adherence score based on the plurality of preceding alimentary elements, wherein the adherence score is related to adherence of a alimentary element program; identifying, by the at least computing device, as a function of the adherence score, an insufficiency of an alimentary element of the of the plurality of preceding alimentary elements; and generating, by the at least computing device, an alimentary instruction set of an alimentary element program, wherein the alimentary instruction set addresses the insufficiency.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an alimentary element prediction machine-learning model. In an embodiment, the system includes a computing device which may provide, to a user, compatible alimentary elements as a function of user biochemistry. Computing device is configured to determine training data describing which alimentary elements the user selected as a function of the alimentary elements that were presented and use this training data to train a computer model to predict user selection. Computing device is configured to generate an alimentary profile as a function of the computer model and may present the user with modulated alimentary elements aimed at improving user physiology as a function of the alimentary profile and an alimentary element program.

Figure 1:
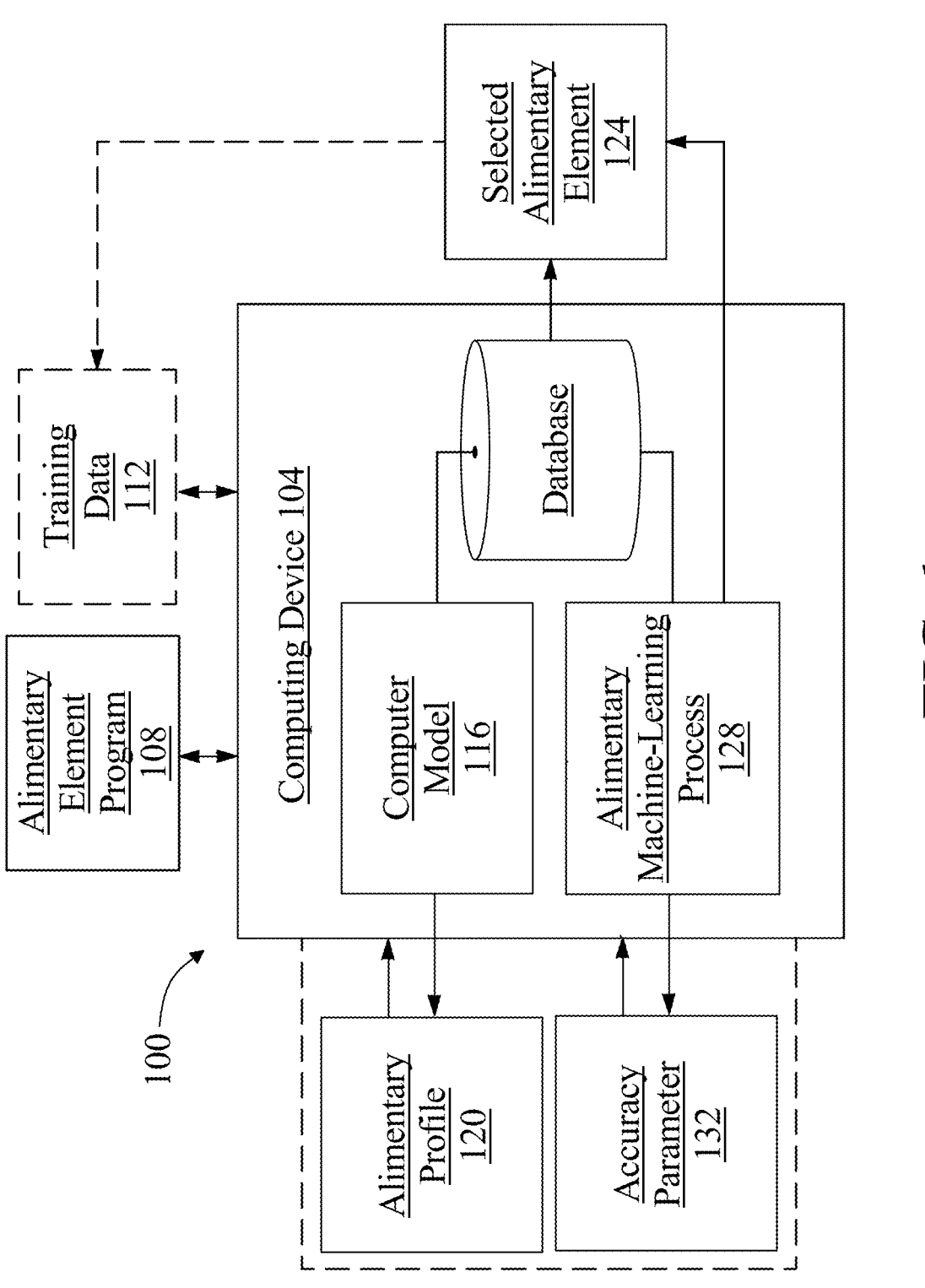
FIG. 1 is a block diagram illustrating a system of user alimentary element learner.

Referring now to FIG. 1, an exemplary embodiment of a system 100 for generating an alimentary element prediction machine-learning model is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing in reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is configured to provide, to a user, a plurality of compatible alimentary elements as a function of a user biochemistry. As used in this disclosure, an "alimentary element," is a meal, grocery item, food element, beverage, nutrition supplement, edible arrangement, or the like, that may be generated by a restaurant, cafeteria, fast food chain, grocery store, food truck, farmer's market, proprietor, convenience store, deli, or any place that provides the above to an individual. A "compatible alimentary element," as used in this disclosure, is an alimentary element provided to an individual according to the individual's biological data, chemical data, physiological data, medical data, and the like. A compatible alimentary element may include alimentary elements intended to address a nutrition deficiency, reduce inflammation, improve recovery from exercise, improve overall health, among other targeted effects. A compatible alimentary element may include alimentary elements provided as a function of an individual's allergies, food intolerances, philosophical, religions, and lifestyle considerations, among other factors involved in selecting alimentary elements. Compatible alimentary elements may be determined for a user as a function of that user's biochemistry. A compatible alimentary element may be generated and provided to a user as a function of a user's biochemistry, such as blood chemistry, for instance blood protein and enzyme concentrations and specific activities for instance of fibrinogen, ferritin, serum amyloid A, $\alpha$-1-acid glycoprotein, ceruloplasmin, hepcidin, haptoglobin, tumor necrosis factor-$\alpha$ (TNF-$\alpha$), among other acute phase proteins; for instance cytokine identities and concentrations for instance interleukin-6 (IL-6); blood metabolites identities and concentrations such as blood sugar, LDL and HDL cholesterol content; hormone identities and concentrations such as insulin, androgens, cortisol, thyroid hormones, and the like; erythrocyte sedimentation rate, blood cell counts, plasma viscosity, and other biochemical, biophysical, and physiological properties regarding blood panels, blood tests, and the like, as it relates to biomarkers of inflammation. Alimentary elements may be recommended to a user as a function of these biochemical data with the intention of modifying the biochemical data, for instance by lowering blood sugar, decreasing LDL cholesterol levels, reducing pro-inflammatory biomarkers, reducing free radicals and oxidative damage, among other targeted effects of alimentary elements on user biochemistry. For instance, biomarkers of inflammation may include biochemical properties specific to a user such as the level of inflammation as evidence by the presence and concentration of inflammatory biomarkers, post-translational modification of proteins, epigenetic markers, etc., and alimentary elements may be identified and provided to a user to focus on reducing inflammation for instance and without limitation, as described in U.S. Nonprovisional application Ser. No. 17/007,251 filed Aug. 31, 2020 titled "METHOD OF SYSTEM FOR REVERSING INFLAMMATION IN A USER," the entirety of which is incorporated herein by reference. The level of inflammation, or any biochemical ailment and/or property of a user may be enumerated, and based on the numerical value, an alimentary element may be recommended to the user. Alternatively or additionally, user biochemistry may be used for determining alimentary element recommendations that improve the user's health state based on the user's biochemistry, for instance and without limitation, as described in U.S. Nonprovisional application Ser. No. 16/375,303 filed Apr. 4, 2020, titled "SYSTEMS AND METHODS FOR GENERATING ALIMENTARY INSTRUCTION SETS BASED ON VIBRANT CONSTITUTION GUIDANCE," the entirety of which is incorporated herein by reference.

Continuing in reference to FIG. 1, computing device 104 providing the plurality of compatible alimentary elements may include retrieving the plurality of compatible alimentary elements from an alimentary element program as a function of user biochemistry. As described above, compatible alimentary elements may be provided to a user as a function of a user's individual alimentary element program, which may be informed by a user's biochemistry data. An "alimentary element program," as used in this disclosure, is a plurality of alimentary elements that a user may be informed to select based on a user's biochemistry, including medical data, physiology, demographics, lifestyle, and the like. An alimentary element program 108 may include, for instance and without limitation, an instruction set that a computing device 104 may provide to a user concerning alimentary elements that may improve the user's health state. An alimentary element program 108 may include alimentary elements a user is expected to substitute to avoid ailments such as allergies, food intolerances, inflammation, and the like. An alimentary element program 108 may include alimentary elements a user is expected to include in their diet to address nutrition deficiencies, symptoms, diseases, and the like. In non-limiting illustrative examples, an alimentary element program 108 may be associated with an audiovisual notification, wherein the notification is used by computing device 104 to provide a compatible alimentary element obtained from the alimentary element program 108 directed to be displayed to the user via a user device, such as a "smartphone", laptop, tablet computer, internet-of-things (IOT) device, and the like. An alimentary element program 108 may include alimentary element instructions, as described in U.S. Nonprovisional application Ser. No. 16/375,303, filed on Apr. 4, 2019, and entitled "SYSTEM AND METHODS FOR GENERATING ALIMENTARY INSTRUCTION SETS BASED ON VIBRANT CONSTUTIONAL GUIDANCE," the entirety of which is incorporated herein by reference.

Continuing in reference to FIG. 1, computing device 104 is configured to receive training data relating to temporally preceding alimentary elements as a function of the plurality of compatible alimentary elements presented to a user. As used in this disclosure, "temporally preceding alimentary elements," are past alimentary elements that a user has selected, indicated, or otherwise obtained from the compatible alimentary elements provided to that user. Such alimentary elements are "temporally preceding" in that they were selected prior in time to the current compatible elements being provided to the user. Alimentary elements may have been selected by user out of a totality of compatible alimentary elements that may have been provided to a user. For instance and without limitation, if an alimentary element program 108 for a user is focused on a ketogenic diet to reduce sugar intake, the selected alimentary elements of the totality of compatible elements provided to the user may include high-fat, high-protein, alimentary elements that lacking in dairy and other milk-based products.

Continuing in reference to FIG. 1, computing device 104 may receive training data corresponding to a respective user interaction with a user device, wherein training data comprises a plurality of user selections of alimentary elements from the plurality of compatible alimentary elements. User selection of alimentary elements may be collected and/or received via a user device. A user device may include a "smartphone", mobile phone, laptop, tablet computer, internet-of-things (IOT) device, or any other device capable of wireless communication such as via the Internet, Bluetooth, cellular network, and the like. User selection of alimentary elements may include receiving food orders submitted via a mobile application and/or web-based input via the Internet to a restaurant website. User selection of alimentary elements may include selections that a user has made via a graphical user interface (GUI) on a user device. User selection of alimentary elements may be received by computing device 104 through direct communication with an application or web-browser by using for instance a "plug-in", "add-on", "extension", or other computer software that adds new functions to a program (internet browser), such as caching web browser alimentary element ordering via a web browser and the Internet. User selection of alimentary elements may be stored and/or retrieved from a database. for instance by generating a data structure from the alimentary element selection from a user's alimentary element program 108. In such an instance, the data structure may include the totality of alimentary elements in the alimentary element program 108, which were provided to the user, which were selected of those that were provided, identifiers about the alimentary element, including the times they were selected, among other data.

Continuing in reference to FIG. 1, as used in this disclosure, "training data" is data regarding user selection of alimentary elements via an interface. Training data 112 may include user alimentary element selection data from an alimentary element program 108. Training data 112 may include alimentary elements the user has selected from ordering online or at an alimentary element establishment, for instance for take-out, delivery, and/or dine-in. Training data 112 may include user selection of grocery items, nutrition supplements, and/or other alimentary elements user has selected and/or purchased outside of alimentary element program 108. Computing device 104 may determine which user selections of training data correspond to user selections of alimentary elements from the plurality of compatible alimentary elements, and which do not. In any case, training data 112 describing user selections from both compatible alimentary elements and non-compatible alimentary elements may be useful for predicting alimentary elements by system 100. Computing device 104 may determine which alimentary elements were selected out of the total that were presented to the user.

Continuing in reference to FIG. 1, a "user device" may include any device suitable for user interaction via a graphical user interface. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the user and accept input from the user. Graphical user interface may accept user interaction, wherein user interaction with a user device may include compatible alimentary element selection and/or non-compatible alimentary element selection. A user device may include computing device 104, a "smartphone," cellular mobile phone, computer, laptop, tablet computer, internet-of-things (JOT) device, among other devices. User device may include any device that is capable to ordering alimentary elements via a data network technology such as 3G, 4G/LTE, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, NFC, etc.), and the like.

Continuing in reference to FIG. 1, training data 112 may include an identification datum for each selection of the plurality of temporally preceding alimentary elements. Computing device 104 may determine user-selected alimentary element identities from a plurality of selections user made, for instance which were 'compatible alimentary elements' and which were not based on the identification datum. Identification datum may include any data that identifies an alimentary element, including the name, price, nutrition facts, ingredients, and the like. Computing device 104 may determine identification datum from signifiers, labels, identifiers, and the like associated with an alimentary element, including the alimentary element producer, branding, distinguishing features, and other data associated with an alimentary element.

Continuing in reference to FIG. 1, training data 112 may include a timestamp for each selection of the plurality of temporally preceding alimentary elements. A "timestamp," as used in this disclosure, is a time associated with the user's selection and/or ordering of an alimentary element. Computing device 104 may determine timestamps involved in alimentary element selection by retrieving times for ordering delivery, dine-in, takeout, or the like, from a mobile application, receipt, bank statement, or the like. For instance and without limitation, computing device 104 may determine that alimentary elements are selected at particular time(s) for particular meal types, for instance and without limitation, breakfast always between 7 am and 8 am. Training data 112 may include identifying information regarding the plurality of alimentary elements, such as meal-type category (breakfast, lunch, dinner, etc.), for instance as it relates to the time the selections are made.

Continuing in reference to FIG. 1, training data 112 corresponding to the respective user interaction with the user device may include generating training data, wherein the training data comprises training data containing the user-selected alimentary elements from the plurality of compatible alimentary elements Computing device 104 may generate "machine-learning training data" from user training data 112. As used in this disclosure, "machine-learning training data" is data containing correlations that a machine-learning process may use to model relationships between two or more categories of data elements. For instance, and without limitation, machine-learning training data may include a plurality of data entries, each entry representing a set of data elements that were recorded, received, and/or generated together; data elements may be correlated by shared existence in a given data entry, by proximity in a given data entry, or the like. Multiple data entries in such training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes, as described in further detail below. Training data may be formatted and/or organized by categories of data elements, for instance by associating data elements with one or more descriptors corresponding to categories of data elements, for instance categorized by timestamps of selection, meal types, ingredient categories, and the like. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data, as described for use in machine-learning processes in further detail below.

Continuing in reference to FIG. 1, computing device 104 is configured to train, using a machine-learning process, a computer model as a function of the user-selection training data to predict user-selectable alimentary elements. Computing device may train a computer model, such as a machine-learning model, with training data that corresponds to elements of training data 112. A machine-learning model may include any machine-learning algorithm, process, or the like, as described in further detail below. Correspondingly, a machine-learning process may be any machine-learning algorithm performed by a machine-learning module, as described in further detail below. Training the computer model 116 to predict user selection category as a function of the training data may include training the computer model 116 as a function of training data that includes a plurality of entries wherein each entry models alimentary element selection to data related to the compatible alimentary elements provided to the user. Computer model 116 may be generated by training a machine-learning model as a function of training data that includes training data 112, wherein the training data 112 is categorized in a variety of ways. A computer model 116 trained in such a way may generate outputs that predict future user alimentary element selections. With continued use of system 100 by user, computing device 104 may generate larger training data sets for training the computer model 116, which may result in more robust predictions.

Continuing in reference to FIG. 1, trained computing model 116 may determine user selection category. The "selection category," as used in this disclosure, is a differentiating factor used to categorize, and discriminate between, alimentary element selections based on categorical data describing the alimentary elements. Selection category may include meal-type, for instance 'breakfast-type' alimentary elements, 'dinner-type' alimentary elements, and the like. Selection category may include price-ranges of alimentary element selections. Selection category may include categorization of alimentary elements as a function of ingredients, diet, producer, time availability, location, budget, nutrition facts, alimentary element program, among other differentiating factors to categories user selections of alimentary elements. Selection category may include cuisine types such as "Mexican food," "Japanese food," etc. Selection category may include diet types such as "low sugar," "ketogenic," "Paleo diet," and the like.

Continuing in reference to FIG. 1, computing device 104 may generate an alimentary profile as a function of the computer model 116. An "alimentary profile," as used in this disclosure, is a profile generated by training data 112 categorized according to patterns, heuristics, correlations, and/or any other relationships present in training data 112 useful for predicting user selections. Alimentary profile 120 may include meal types, order times, ingredients, dietary information, locations, prices, and the like. In non-limiting illustrative examples, alimentary profile 120 may include data from the computer model 116 illustrating that a user will choose a plant-based meal over a meal that contains animal products 66% of the time. Such patterns, heuristics, correlations, etc. data in an alimentary profile 120 may be useful in predicting how to guide presentation of compatible alimentary elements to a user. Alimentary profile 120 may be useful to system 100 for 'knowing' which compatible alimentary elements form the alimentary element program to show the user, at which times, what types of meals, etc., and which alimentary elements a user is likely to select out of what is displayed.

Continuing in reference to FIG. 1, the alimentary profile 120 may include a plurality of predicted alimentary elements based on the training data 112 and the computer model 116. Alimentary profile 120 may include determinations from computer model 116, including predicted user selections of alimentary elements in the form of meals, grocery items, etc. Computing device 104 may determine an alimentary profile 120 that contains a quantification, such as a percentage likelihood (among other metrics), predicting or otherwise expressing predicted likelihood a user will select a compatible alimentary element. Such metrics may be displayed to user, or simply used by computing device 104 to 'know' which alimentary elements to display from alimentary element program 108. Alimentary profile 120 may comprise alimentary elements a user is predicted to select, and metrics associated with the likelihood of selection provided to the user device. Alimentary profile 120 may contain at least a selected alimentary element, indicating a compatible alimentary element a user is predicted to select.

Continuing in reference to FIG. 1, computing device 104 is configured to receive a user input for an alimentary element. A "user input," as used in this disclosure, is a request made by the user for an alimentary element. A user input may include a request for an alimentary element recommendation from the alimentary element program 108. A user input may include input via a user device, including the computing device 104, that designates an alimentary element and/or or a recommendation for using a particular alimentary element, for instance as part of a meal. A user input for an alimentary element may include a request for a recipe from an alimentary element program 108. A user input for an alimentary element may include a request for an alimentary element the user may order as take-out while maintaining a particular diet. User may indicate via a graphical user interface, for instance through a user device, an input for an alimentary recommendation. An "alimentary recommendation," as used in this disclosure, is a compatible alimentary element recommended to the user as designated by user request. Computing device 104 may receive such an input for an alimentary recommendation wherein the computing device 104 may categorize the request based on time, meal-type, etc. For instance and without limitation, if a user generally selects lunch items between 11:30 am and 2:00 pm, a request for an alimentary recommendation to computing device 104 at 11:45 am may be associated with returning compatible alimentary elements that are "lunch items", despite a user not indicating "lunch". Alternatively or additionally, user may indicate directly to computing device 104 a request by textual submission, graphical icon selection, or any other manner compatible with a graphical user interface, which indicates such a request.

Continuing in reference to FIG. 1, computing device 104 may generate a selected alimentary element, which includes retrieving, from the alimentary element program 108, a plurality of selected alimentary elements as a function of the alimentary profile 120 and determining, using an alimentary selection machine-learning process, a plurality of accuracy parameters for the plurality of selected alimentary elements. A "selected alimentary element," as used in this disclosure, is a compatible alimentary element a user is predicted to select as an output from system 100. Selected alimentary element may be simply referred to as an "alimentary element" that represent an output of system 100. Selected alimentary element 124 may include "predicted alimentary elements," output by the computer model 116 and machine-learning process as part of the alimentary profile 116. Computing device 104 may retrieve (for instance from an alimentary element program 108 stored in a database) a plurality of selected alimentary elements 124, using the alimentary profile 120 to inform a query of the database. Alternatively or additionally, computing device 104 may use an alimentary machine-learning process 128 to retrieve such selected alimentary elements 124. Alimentary machine-learning process 128 may be any machine-learning algorithm and/or process performed by computing device, as described in further detail below. Alimentary machine-learning process 128 may accept an input of an alimentary profile 120 and a user input for an alimentary element and retrieve a plurality of selected alimentary elements 124 as a function of the alimentary profile 120 and the request. Alimentary machine-learning process 128 may then determine for the plurality of selected alimentary element 124 a plurality of accuracy parameters.

Continuing in reference to FIG. 1, an "accuracy parameter," as used in this disclosure, is a quantitative and/or qualitative metric that describes the accuracy of an alimentary element for a user. An accuracy parameter 132 may include a metric or numerical value that quantifies the accuracy of a predicted alimentary element for a particular user. An accuracy parameter 132 may include a metric that quantifies the how well the user is predicted to enjoy or otherwise select an alimentary element. An accuracy parameter 132 may include qualitative measures such as a "yes/no" that indicated a selected alimentary element 124 will be selected or not. An accuracy parameter 132 may include quantitative measures such as a percentage likelihood of selection, a score that ranges on a scale from a higher numerical value to a lower numerical value, where the numerical value indicates likelihood of selection. An accuracy parameter 132 may include a description of the 'appropriateness' of a selected alimentary element 124 for user selection depending on the time of day, meal-type, price, etc.

Continuing in reference to FIG. 1, alimentary machine-learning process 128 may rank, using a ranking function, the plurality of selected alimentary elements 124 as a function of their associated accuracy parameters 128. A ranking function may be a scoring index, weighting function, or the like, that ranks an input (such as selected alimentary elements 124) using a ranking criterion (accuracy parameter 132) to provide an output that is a logical numerical listing of the inputs. Computing device 104 may use alimentary machine-learning process 128 to rank selected alimentary elements 124; alternatively or additionally, computing device 104 may use any other suitable machine-learning process as described in further detail below to generate the ranking. Correspondingly, computing device 104 may additionally 'decide' to present selected alimentary elements 124 as a function of the ranking. For instance and without limitation, system 100 may generate thousands of selected alimentary elements 124 the user is predicted to select but may choose to present the top 10 in a category, present by relative distance to user, present by price, and/or present by other criteria. Ranking criteria, for instance and without limitation, may include time-of-day, meal-type, diet-type, or other discriminating factors, for knowing when to fine-tune predicted alimentary element selection by the user.

Continuing in reference to FIG. 1, the alimentary profile 120 may include an accuracy parameter 128 for each predicted element from the computer model 116. Computing device 104 may 'know' which 'type' of alimentary element to retrieve from the alimentary element program 108 based on the accuracy parameter associated with the predicted element. A "predicted element" may include any alimentary element the trained computer model 116 has indicated as a candidate predicted user-selectable alimentary element. Alimentary profile 120 may include a numerical value accuracy parameter 128 associated with a category for each alimentary element in the alimentary element profile 120. For instance, an alimentary element may be 89% accurate for a user for a lunch selection, but only 35% accurate for a breakfast selection. Accuracy parameter 128 may be useful to computing device 104 for timing which alimentary elements and which type of alimentary elements to provide a user upon receive a user request for an alimentary element.

Continuing in reference to FIG. 1, computing device 104 is configured to present, as a function of the user input, the alimentary element as a function of the alimentary profile 120. Computing device 104 may present a selected alimentary element 124 as a function of the alimentary profile 120 and the plurality of compatible alimentary elements. Computing device 104 may retrieve compatible alimentary elements from an alimentary element program 108, for instance and without limitation, from a database such as a NoSQL database, relational database, online repository such as a cloud-based data store, or the like. Computing device 104 may retrieve compatible alimentary elements from an alimentary element program 108 stored locally, for instance in non-transitory computer readable storage medium accessed by a mobile application, GUI, or the like, functioning on computing device 104 and/or user device. Computing device 104 may retrieve selected alimentary elements 124 from alimentary element program 108 as a function of the alimentary profile 120. For instance, computing device 104 may query for compatible alimentary elements using accuracy parameters, rankings, and the like, to 'learn' which alimentary elements should be presented to user at a particular time, meal, location, etc.

Continuing in reference to FIG. 1, receiving the user input for the alimentary element may include using the computing device 104 to retrieve the alimentary element from the alimentary element program 108 as a function of the outputs from the computer model 116 and the machine-learning process. Computing device 104 may generate, via a graphical user interface, a representation of at least the alimentary, wherein the representation changes as a function of user interaction. For instance and without limitation, user interaction may include viewing the compatible alimentary element options, not selecting one, leaving the display or alimentary elements, and returning sometime later. In such an instance, reluctance by the user to select an alimentary element may initiate a change in the representation of at least a single alimentary element, wherein the representation is different the next time the user returns to the interface. In further non-limiting illustrative examples, user selecting a "Jamaican meal," for lunch may prompt the removal of "Jamaican food" for dinner, but may increase the likelihood that "Jamaican meal," is displayed for lunch in the future. Alimentary element representation may change as a function of user current location, wherein if some alimentary elements are not feasibly obtainable where a user is located, the representation may change.

Continuing in reference to FIG. 1, computing device 104 presenting a selected alimentary element 124 may include altering one or more alimentary elements provided as a function of the alimentary profile 120. Computing device 104 providing, to a user, a plurality of compatible alimentary elements, as described above, may alter what is provided to the user as a function of the alimentary profile 120. Altering the compatible alimentary elements provided may include altering as a function of accuracy parameters. Altering may include changing one or more alimentary elements provided to a user as a function of the time of selection by the user, wherein the alimentary profile 120 may include selection patterns based on time. Altering may include changing the presentation of alimentary elements each time a user interacts with computing device 104, opens a mobile application, changes location, or the like.

Continuing in reference to FIG. 1, altering one or more alimentary elements may include generating, via a graphical user interface, a representation of at least a selected alimentary element 124 and providing the representation to the user. Computing device 104 may alter one or more alimentary elements represented via the graphical user interface as a function of the alimentary profile 120, accuracy parameters, compatible alimentary element rankings, and the like. Computing device 104 may 'start' with generating a representation of a variety of compatible alimentary elements but alter the representation as a function of user input. User input may be textual-based input, scrolling and/or navigating without selection, and/or selection of certain alimentary elements, among other user input. Computing device 104 may then alter the representation, using the user input, to build the alimentary profile 120 and personalize the representation via the graphical user interface. Personalization may include altering alimentary elements displayed to user by generating a representation of alimentary elements above a particular threshold value of accuracy parameter.

Continuing in reference to FIG. 1, computing device 104 may generate training data 112 for the computer model 116 as a function of user interaction from the representation. The altering one or more alimentary elements may be used as training data 112 to train computer model 116 to better understand "when" and in what manner to change the representation of alimentary elements for a user.

Still referring to FIG. 1, in some embodiments computing device 104 may be configured to output compatible alimentary elements related to alimentary element program, wherein alimentary element program is configured to address nutritional deficiencies based on the biochemistry of the user by supplementing alimentary elements previously recommend to the user. Computing device 104 may receive preceding alimentary elements and timestamps, as described above, and use a machine-learning process as described throughout this this disclosure, to evaluate and score each preceding alimentary element to accuracy parameter 132 to generate a adherence score. An "adherence score," as use herein is the cumulative scoring of alimentary elements. The adherence score may reflect a user's overall adherence to an alimentary element program. For example, an alimentary element program may be configured to address a calcium deficiency, wherein past user selection of alimentary elements may be evaluated to see if alimentary elements selected eradicate, placate, or worsen the deficiency. Computing device 104 may track selections of alimentary over a broad or narrow period of time. For example, computing device 104 may track on a daily, weekly, or monthly basis. In some embodiments, computing device may train an adherence classier using training data 112. Training data 112 may correlate alimentary elements to an accuracy parameter related to an alimentary element program. The adherence classifier may be trained to receive the plurality of preceding alimentary elements as an input and output each preceding alimentary element matched to accuracy parameter 132, wherein computing device 104 may aggregates the score to output the adherence score. In some embodiments, adherence classifier may be trained to aggregate the matches and output the adherence score.

Still referring to FIG. 1, computing device 104 may identify an insufficiency of an alimentary element of the of the plurality of preceding alimentary elements in relation to the alimentary element program. Insufficiency may relate to non-selected compatible elements part of alimentary element program previously recommended or presented to user that were not selected often or at all. Insufficiency may relate to preceding alimentary elements matched to a low accuracy parameter. Computing device 104 may train a insufficiency classifier configured to receive the outputs of the adherence classifier and the adherence score as an input and output identified alimentary elements nonadherent to the alimentary element program. Nonadherence may relate to alimentary elements commonly selected but the user that does not address or hinders improvement of a nutritional deficiency. Nonadherence may include compatible alimentary elements originally recommended to the user that do not get selected. For example, if preceding alimentary elements show that a user does not select certain vitamins of foods previously recommended to address a calcium deficiency, then computing device 104 may flag the non-selected compatible alimentary elements as nonadherent to the alimentary element program. Training data for the insufficiency classifier may include training data 112 including data correlating non-selected compatible alimentary elements to nonadherence parameters. A "nonadherence parameter," as used herein is a metric representing the impact on an alimentary element program. For example a nonadherence parameter may represent a low percentage of calcium consumed by a user in relation to the actual percentage needed to overcome a calcium deficiency. In some embodiments, identifying an insufficiency of an alimentary element may include ranking alimentary elements based on an accuracy parameter and or a nonadherence parameter using ranking methods as described above.

Still referring to FIG. 1, in some embodiments, computing device 104 may generate an alimentary instruction set part of the alimentary element program, as described above, addressing the insufficiency/nonadherence. An alimentary instruction set may reflect an applicable solution to nourishment requirements, health deficiencies, and other applicable factors associated with the health, nutrition, and wellness of a user. For example, computing device 104 may supplement non-selected alimentary elements with compatible alimentary elements similar to the preceding alimentary elements, but adhere to the alimentary element program. For example, preceding alimentary elements may show a user commonly selects ice cream as an alimentary element. Computing device 104 may supplement "ice cream," with "yogurt," wherein the yogurt may have more of a positive impact on the alimentary element program. Computing device 104 may transmit the alimentary instruction set to a user using methods as described above, for example, a though a GUI.

Figure 2:
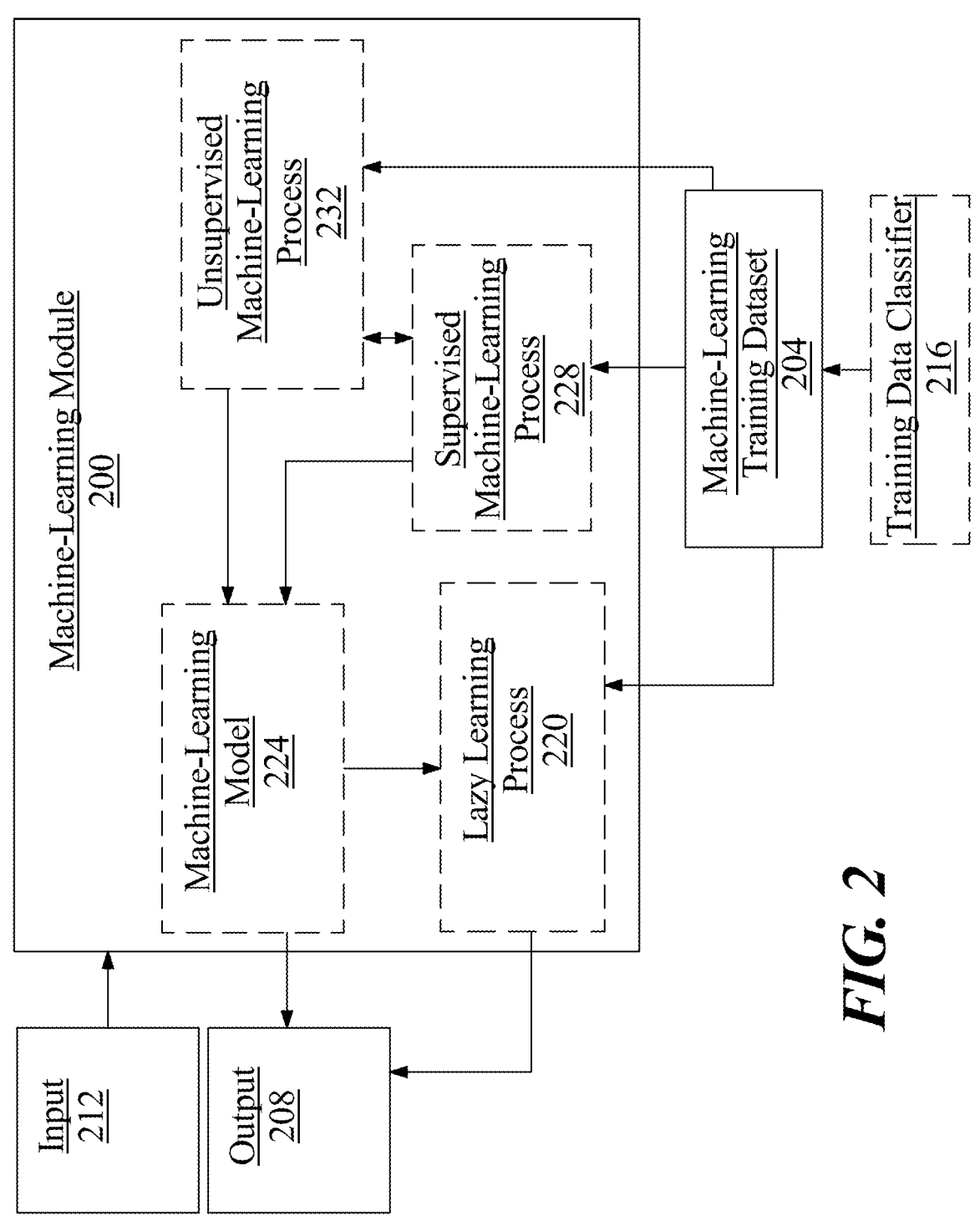
FIG. 2 is a block diagram illustrating an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses machine-learning training dataset 204, as described above, to generate an algorithm that will be performed by a computing device/module to produce outputs 208 given data provided as inputs 212; this is in contrast to a non-machine learning software program where the commands to be executed are determined in advance by a subject and written in a programming language.

Alternatively or additionally, and continuing to refer to FIG. 2, machine-learning training dataset 204 may include one or more elements that are not categorized; that is, machine-learning training dataset 204 may not be formatted or contain descriptors for some elements of data. Machine-learning algorithms and/or other processes may sort machine-learning training dataset 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same machine-learning training dataset 204 to be made applicable for two or more distinct machine-learning algorithms as described in further detail herein. Machine-learning training dataset 204 used by machine-learning module 200 may correlate any input data as described in this disclosure to any output data as described in this disclosure.

Further referring to FIG. 2, machine-learning training dataset 204 may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from machine-learning training dataset 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of compatible alimentary elements based on meal-type (breakfast, lunch, dinner), ingredient lists, diet type, time of selection, and the like, and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of machine-learning training dataset 204. Heuristic may include selecting some number of highest-ranking associations and/or machine-learning training dataset 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a machine-learning training dataset 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a alimentary profile 120 and an alimentary element program 108, as described above as inputs, accuracy parameters as outputs, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output. Ranking function may be expressed as a risk function representing an "expected loss" of an algorithm relating inputs to outputs, where loss is computed as an error function representing a degree to which a prediction generated by the relation is incorrect when compared to a given input-output pair provided in machine-learning training dataset 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include the least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a machine-learning training dataset 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using machine-learning training dataset 204.

Figure 3:
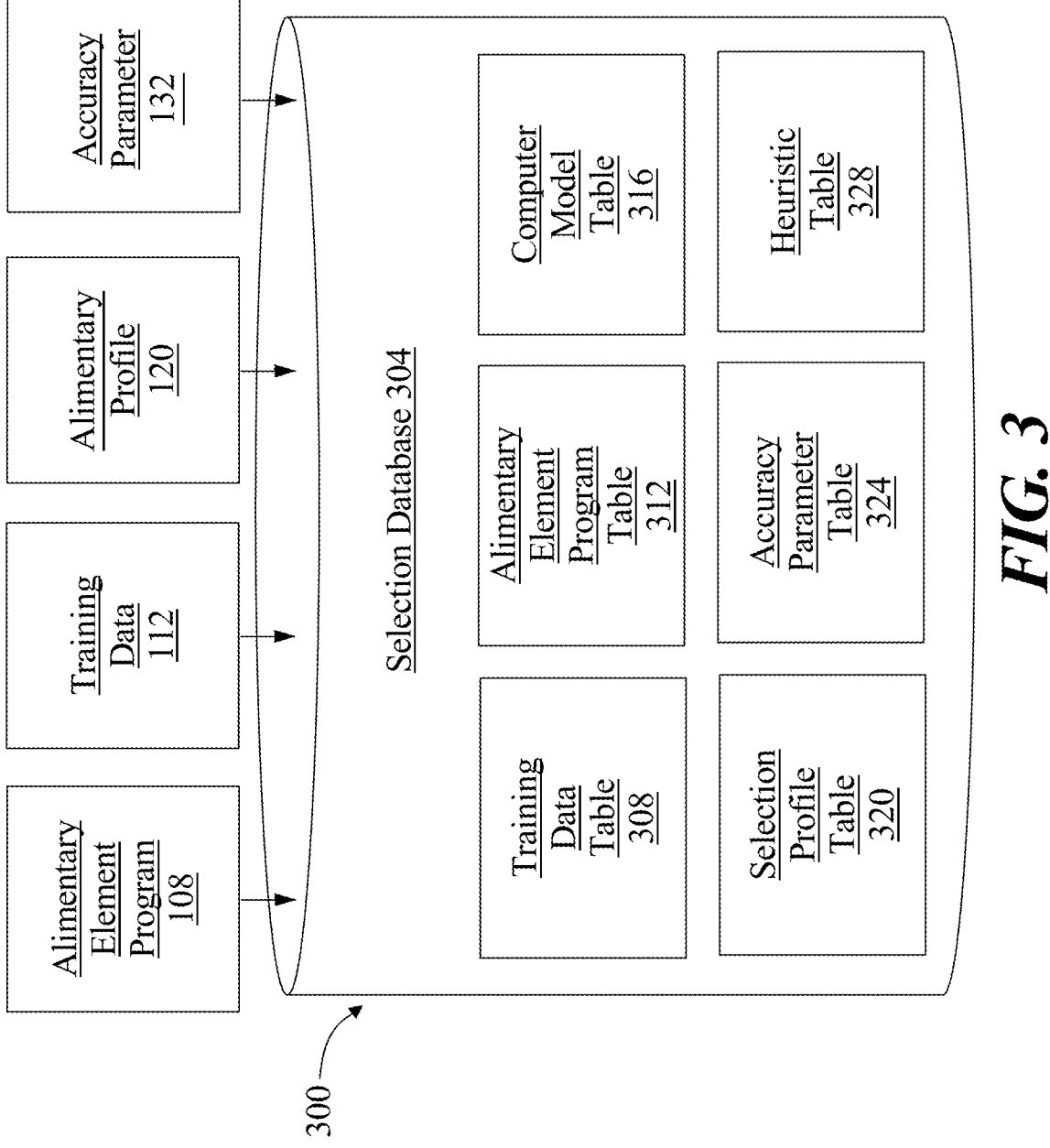
FIG. 3 is a block diagram illustrating an exemplary embodiment of an alimentary database.

Referring now to FIG. 3, a non-limiting exemplary embodiment 300 of a selection database 304 is illustrated. Selection database 304 may be implemented, without limitation, as a relational database, a key-value retrieval database such as a NOSQL database, or any other format or structure for use as a database that a person skilled in the art would recognize as suitable upon review of the entirety of this disclosure. Selection database 304 may alternatively or additionally be implemented using a distributed data storage protocol and/or data structure, such as a distributed hash table and the like. Selection database 304 may include a plurality of data entries and/or records, as described above. Data entries in an selection database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. Computing device 104 may store and/or retrieve any determinations, as described herein, from the selection database 304, such as a, alimentary element program 108, training data 112 including selected alimentary elements 124, alimentary elements provided by not selected, compatible alimentary elements, computer model 116 (including any determinations, models, heuristics, relationships, function, and the like), alimentary profile 120, accuracy parameters 128 (and associated rankings).

Further referring to FIG. 3, selection database 304 may include, without limitation, and training data table 308, alimentary element program table 312, computer model table 316, alimentary profile table 320, accuracy parameter table 324, and/or heuristic table 328. Determinations by a machine-learning process, machine-learning model, and/or ranking function, may also be stored and/or retrieved from the selection database 304, for instance in non-limiting examples a classifier describing a plurality of training data 112 as it relates to a plurality of compatible alimentary elements, wherein a classifier is an identifier that denotes a subset of data that contains a heuristic and/or relationship, as may be useful to system 100 described herein. As a non-limiting example, selection database 304 may organize data according to one or more instruction tables. One or more selection database 304 tables may be linked to one another by, for instance in a non-limiting example, common column values. For instance, a common column between two tables of selection database 304 may include an identifier of a submission, such as a form entry, textual submission, local access addresses, parameters, rankings, metrics and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of an selection database 304 may include, as a non-limiting example, an training data table 308, which may include categorized identifying data, as described above, including compatible alimentary elements that were selected, those that were displayed and not selected, how often a selection was or was not made, and the like. One or more tables may include alimentary element program table 312, which may include data regarding health state and compatible alimentary elements for the health state, including how the compatible alimentary elements may change as a function of time, that system 100 may use to retrieve and/or store for determinations herein. One or more tables may include computer model table 316, which may include a determinations, variables, relationships, functions, classifiers, data, and the like, for instance and without limitation, that system 100 may use to retrieve and/or store predicted alimentary element selections of the user. One or more tables may include alimentary profile table 320, which may include classifiers, selected alimentary elements 124, and the like, as described above for instance and without limitation, that system 100 may use to retrieve. One of more tables may include an accuracy parameter table 324, which may include accuracy parameters, rankings outputs, and the like, organized into subsets of data for system 100. One or more tables may include, without limitation, a heuristic table 328, which may organize rankings, scores, models, outcomes, functions, numerical values, vectors, matrices, and the like, that represent determinations, optimizations, iterations, variables, and the like, include one or more inputs describing potential mathematical relationships, as described herein.

Figure 4:
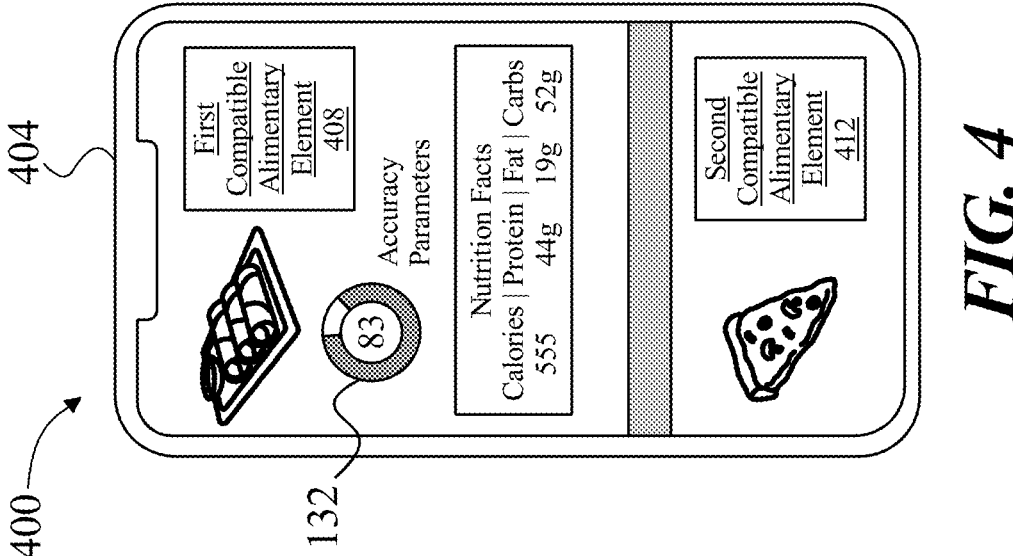
FIG. 4 is a diagrammatic representation illustrating an exemplary embodiment of a user device.

Referring now to FIG. 4, a non-limiting exemplary embodiment 400 of a user device is illustrated. User device 404 may be configured to display a compatible alimentary element from an alimentary element program 108. User device 404 may display a variety of information, for instance and without limitation, nutrition facts, proposed health benefits, the role of the compatible alimentary element in reducing inflammation, disease state, symptoms, and the like. User may select a compatible alimentary element via the user device 404 as a function of any factor. System 100 may then generate an alimentary profile 120, as described above, to alter compatible alimentary elements that are shown based on patterns, relationships, and the like, observed in the training data 112 and captured in the computer model 116. First compatible alimentary element 408 and second compatible alimentary element 412 may represent meals, food items, of the like, that are beneficial to improving the user's health state, as retrieved from an alimentary element program 108 as stored and/or retrieved from the selection database 304. First compatible alimentary element 408 and second compatible alimentary element 412 may represent alimentary elements a user is predicted to select with more favorable accuracy parameters 132 than compatible alimentary elements that would otherwise be presented from alimentary element program 108. As depicted in FIG. 4, the first compatible alimentary element 408 and second compatible alimentary element 412 are dinner suggestions that mimic foods with gluten (egg rolls and pizza), but perhaps are gluten-free options, lack meat products, etc. which may represent healthier options, but nonetheless remain more appetizing to the user over other options contained in alimentary element program 108. In such a case, system 100 may determine these items would be selected over other options, such as a kale salad, but may nonetheless keep user on track for following a healthier diet.

Figure 5:
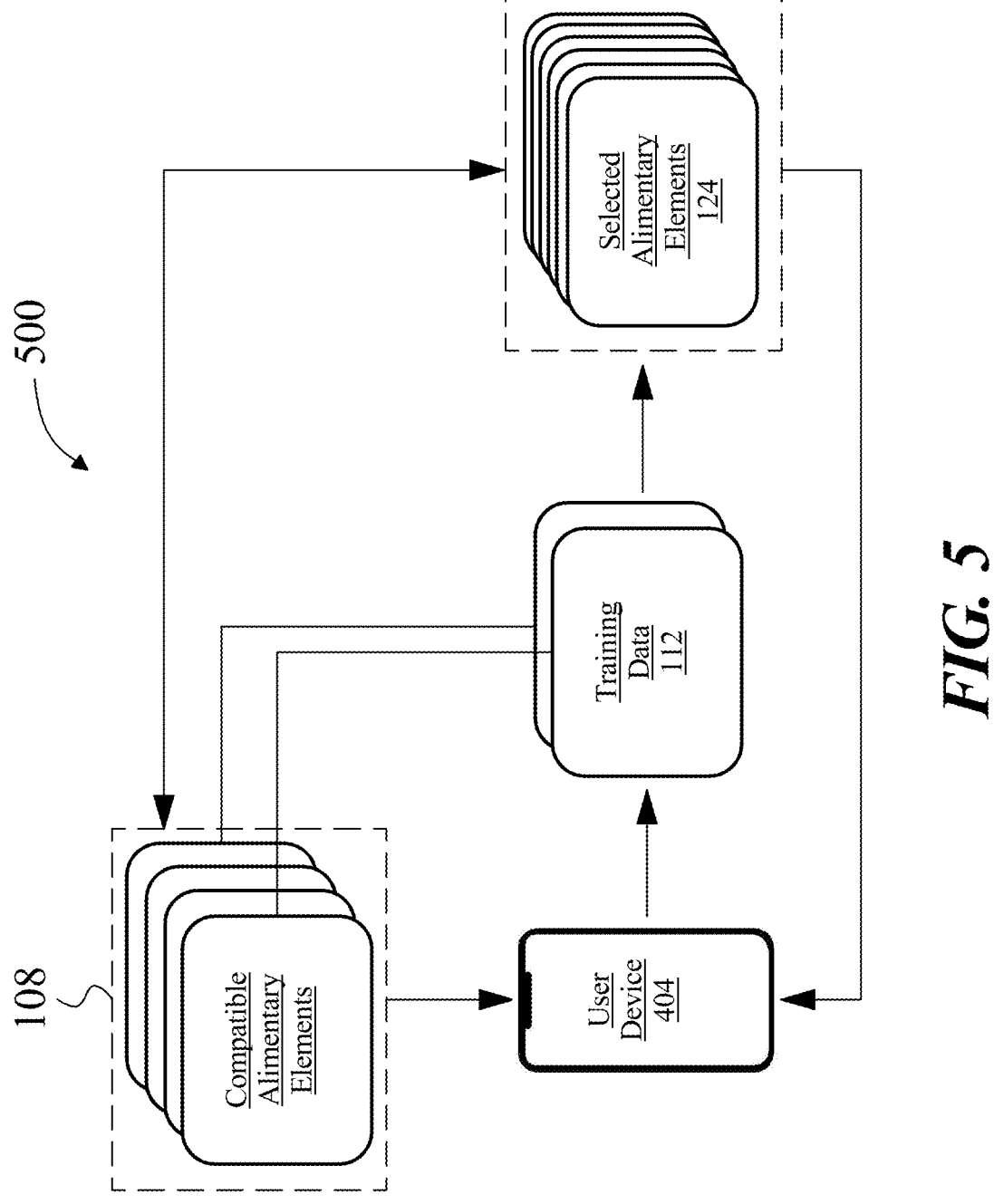
FIG. 5 is a diagrammatic representation illustrating an exemplary embodiment of altering alimentary elements.

Referring now to FIG. 5, a non-limiting exemplary embodiment 500 of altering alimentary elements via the graphical user interface is illustrated. Compatible alimentary elements may be retrieved from an alimentary element program 108 and provided to a user via a user device 404. System 100 may train a computer model 116 to generate an alimentary profile 120 using training data 112 from user selections. Alimentary profile 120 may include a plurality of selected alimentary elements 124. Alimentary machine-learning process 128 may generate an output of accuracy parameters from selected alimentary element 124 inputs in the alimentary profile 120. Alimentary machine-learning process 128 may rank the plurality of selected alimentary elements 124 as a function of the plurality of associated accuracy parameters. System 100 may then alter the alimentary elements provided via the graphical user interface as a function of the alimentary profile 120 and the ranking.

Figure 6:
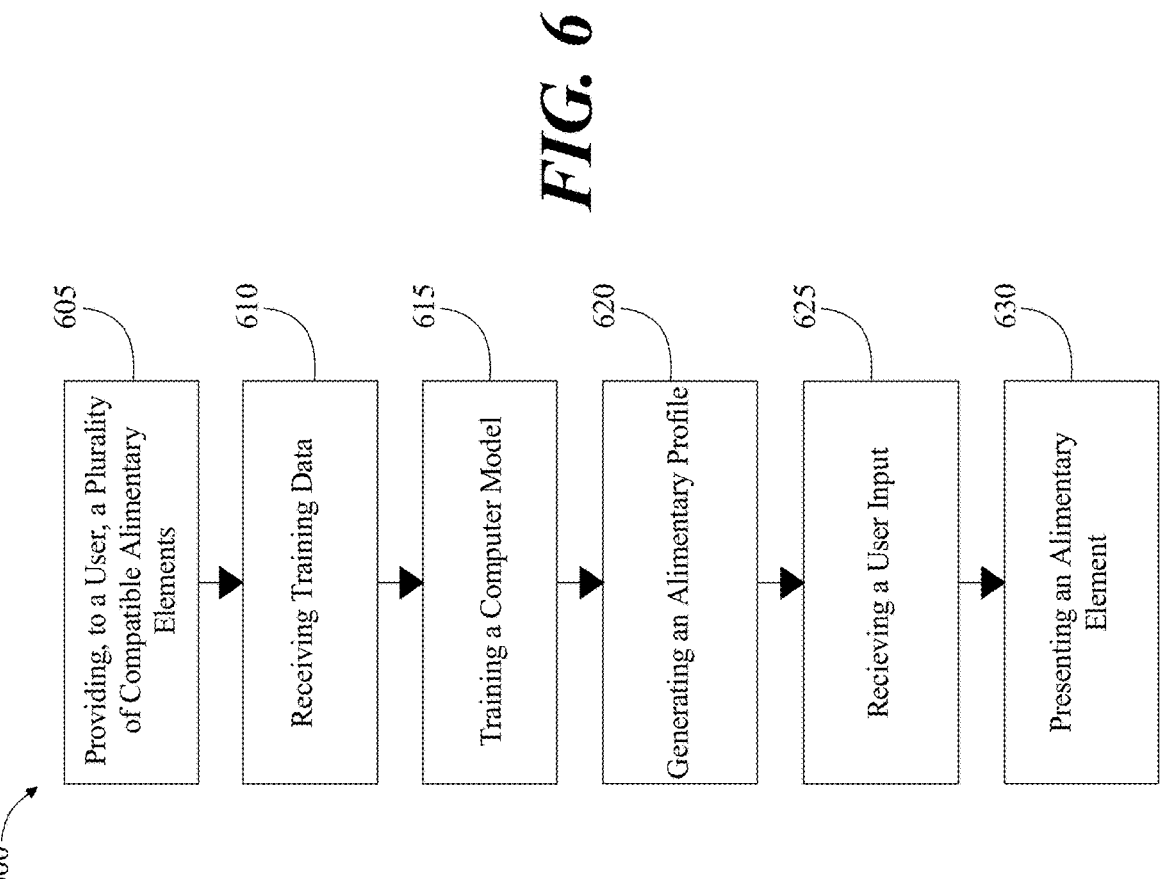
FIG. 6 is a flow diagram illustrating an exemplary workflow of a method of user alimentary element learner.

Referring now to FIG. 6, a non-limiting exemplary embodiment of a method 600 of a user alimentary element learner. At step 605, computing device 104 is configured for providing, by a computing device, to a user, a plurality of compatible alimentary elements as a function of user biochemistry. Providing the plurality of compatible alimentary elements may include retrieving the plurality of compatible alimentary elements from an alimentary element program 108 as a function of user biochemistry; this may be implemented, without limitation, as described above in FIGS. 1-5.

Still referring to FIG. 6, at step 610, computing device 104 is configured for receiving training data 112 relating a plurality of temporally preceding alimentary elements as a function of the plurality of compatible alimentary elements presented to a user. Training data 112 may include an identification datum for each selection of the plurality of temporally preceding alimentary elements. Training data 112 may include a timestamp for each selection of the plurality of temporally preceding alimentary elements. Training data 112 corresponding to the respective user interaction with the user device 404 may include generating training data 112, wherein the training data 112 comprises training data containing the user-selected alimentary elements from the plurality of compatible alimentary elements; this may be implemented, without limitation, as described above in FIGS. 1-5.

Continuing in reference to FIG. 6, at step 615, computing device 104 is configured for training, using a machine-learning process, a computer model 116 as a function of the user-selection training data 112 to generate user-selectable alimentary elements. Training, using the machine-learning process, the computer model 116 to predict user-selected alimentary elements as a function of the user-selected alimentary elements training data may include using the machine-learning process and the training data 112 to generate a trained computer model 116 as a function of training data that includes a plurality of entries wherein each entry models alimentary element selection to data related to the compatible alimentary elements provided to the user; this may be implemented, without limitation, as described above in FIGS. 1-5.

At step 620, and still referring to FIG. 6, computing device 104 is configured for generating an alimentary profile 120 as a function of the computer model 116. The alimentary profile 120 may include a plurality of alimentary elements output based on the training data 112 and the computer model 116. Generating alimentary element may include retrieving, from the alimentary element program 108, a plurality of alimentary elements as a function of the alimentary profile 120, determining, using an accuracy machine-learning process 128, a plurality of accuracy parameters 132 for the plurality of alimentary elements; this may be implemented, without limitation, as described above in FIGS. 1-5.

Continuing in reference to FIG. 6, at step 625, computing device 104 is configured for receiving a user input for an alimentary element. Receiving the user input for the alimentary element may include using the computing device 104 to retrieve the alimentary element from the alimentary element program 108 as a function of the outputs from the computer model 116 and the machine-learning process, and generating, via a graphical user interface, a representation of at least the alimentary, wherein the representation changes as a function of user interaction; this may be implemented, without limitation, as described above in FIGS. 1-5.

Continuing in reference to FIG. 6, at step 630, computing device 104 is configured for presenting as a function of the user input, the alimentary element as a function of the alimentary profile. Computing device 104 may generate training data 112 for the computer model 116 as a function of user interaction from the representation; this may be implemented, without limitation, as described above in FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
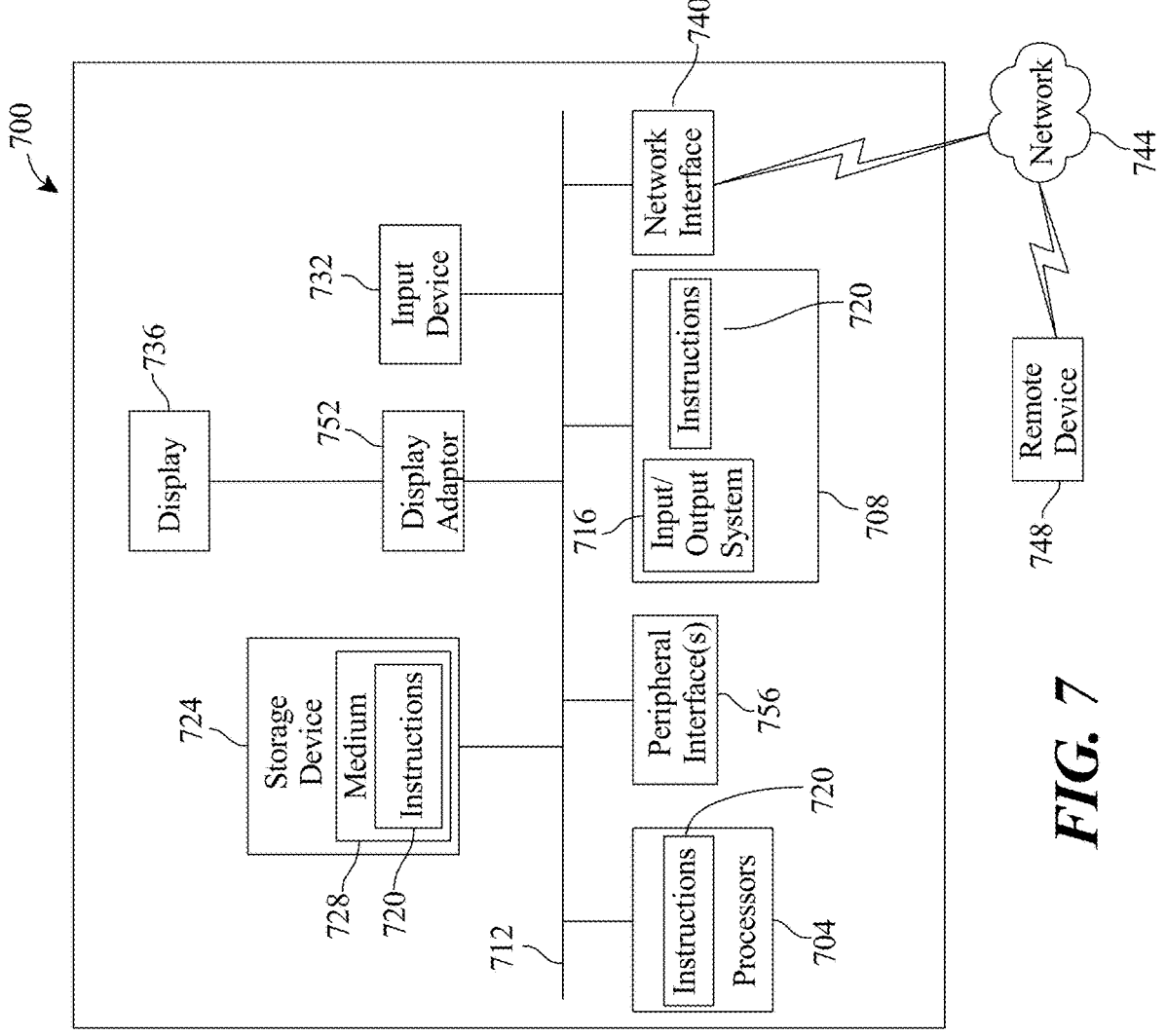
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for identifying an insufficient alimentary element, the system comprising:
   a computing device, wherein the computing device is designed and configured to:
   receive a plurality of preceding alimentary elements;
   generate an adherence score based on the plurality of preceding alimentary elements, wherein generating the adherence score comprises:
   identifying an alimentary element program; and
   generating the adherence score as a function of the alimentary element program and the plurality of preceding alimentary elements utilizing an adherence classifier which further comprises:
   receiving an adherence training data set, wherein the adherence training data set comprises a plurality of alimentary elements correlated to a plurality of accuracy parameters related to one or more alimentary element programs;
   training, iteratively, the adherence classifier using the adherence training data set, the adherence classifier comprising an input layer of nodes, one or more intermediate layers, and an output layer of nodes, wherein training the adherence classifier includes:
   updating the adherence training data set with feedback from previous iterations of the adherence classifier; and
   adjusting connections and weights between adjacent layers of the input layer of nodes, the one or more intermediate layers, and the output layer of nodes based on the updated adherence training data set; and
   generating the adherence score as a function of the trained adherence classifier;
   identify, as a function of the adherence score, an insufficiency of an alimentary element of the of the plurality of preceding alimentary elements;
   generate an alimentary instruction set of the alimentary element program based on the insufficiency, wherein the alimentary instruction set comprises a compatible alimentary element configured to substitute for at least one preceding alimentary element of the plurality of preceding alimentary elements, and wherein generating the compatible alimentary element comprises:
   receiving a training data set comprising a plurality of entries correlating compatible alimentary elements and previous alimentary element selections;
   receiving current user interactions of a user through a graphical user interface, wherein the user interactions comprise one or more compatible alimentary element user-selections and/or one or more non-compatible alimentary element user-selections;
   expanding the training data set as a function of the user interactions;
   generating a classifier as a function of the expanded training data set using a classification algorithm;
   filtering elements of the expanded training data set using the classifier to generate a plurality of training data subsets to categories of compatible alimentary elements by clustering elements together as a function of a distance metric threshold;

selecting at least one filtered training data subset of the plurality of training data subsets as a function of the insufficiency;

training a machine learning model to predict compatible alimentary elements as a function of the filtered training data subset; and generating the compatible alimentary element to address the insufficiency as a function of the machine learning model; and display the compatible alimentary element from the alimentary instruction set using the graphical user interface.

2. The system of claim 1, wherein at least one preceding alimentary element of the plurality of preceding alimentary elements comprises a past alimentary element selected by the user from a plurality of compatible alimentary elements.

3. The system of claim 2, wherein at least a compatible alimentary element of the plurality of compatible alimentary elements comprises an alimentary element intended to address a nutrition deficiency.

4. The system of claim 1, wherein receiving the plurality of preceding alimentary elements further comprises receiving a plurality of timestamps, wherein the plurality of timestamps includes a timestamp associated with each preceding alimentary element of the plurality of alimentary elements.

5. The system of claim 1, wherein generating the adherence score further comprises determining the adherence score as a function of an accuracy parameter.

6. The system of claim 1, wherein identifying the insufficiency of an alimentary element comprises utilizing an insufficiency classifier to output an insufficient alimentary element.

7. The system of claim 6, wherein the insufficiency of the insufficient alimentary element relates a low accuracy parameter matched to the alimentary element.

8. The system of claim 1, wherein the insufficiency relates to non-selected compatible elements part of the alimentary element program.

9. The system of claim 1, wherein the alimentary instruction set comprises a supplement for a non-selected alimentary element.

10. A method for identifying an insufficient alimentary element, the method comprising:

receiving, by at least a computing device, a plurality of preceding alimentary elements;

generating, by the at least computing device, an adherence score based on the plurality of preceding alimentary elements, wherein generating the adherence score comprises:

identifying an alimentary element program; and generating the adherence score as a function of the alimentary element program and the plurality of preceding alimentary elements utilizing an adherence classifier which further comprises:

receiving an adherence training data set, wherein the adherence training data set a plurality of preceding alimentary elements correlated to a plurality of preceding alimentary elements matched to accuracy parameters related to one or more alimentary element programs;

training, iteratively, the adherence classifier using the adherence training data set, the adherence classifier comprising an input layer of nodes, one or more intermediate layers, and an output layer of nodes, wherein training the adherence classifier includes:

updating the adherence training data set with feedback from previous iterations of the adherence classifier; and adjusting connections and weights between adjacent layers of the input layer of nodes, the one or more intermediate layers, and the output layer of nodes based on the updated adherence training data set; and generating the adherence score as a function of the trained adherence classifier;

identifying, by the at least computing device, as a function of the adherence score, an insufficiency of an alimentary element of the of the plurality of preceding alimentary elements;

generating, by the at least computing device, an alimentary instruction set of the alimentary element program based on the insufficiency, wherein the alimentary instruction set comprises a compatible alimentary element configured to substitute for at least one preceding alimentary element of the plurality of preceding alimentary elements and wherein generating the compatible alimentary element comprises:

receiving a training data set comprising a plurality of entries correlating compatible alimentary elements and previous alimentary element selections;

receiving current user interactions of a user through a graphical user interface, wherein the user interactions comprise one or more compatible alimentary element user-selections and/or one or more non-compatible alimentary element user-selections;

expanding the training data set as a function of the user interactions;

generating a classifier as a function of the expanded training data set using a classification algorithm;

filtering elements of the expanded training data set using the classifier to generate a plurality of training data subsets to categories of compatible alimentary elements by clustering elements together as a function of a distance metric threshold;

selecting at least one filtered training data subset of the plurality of training data subsets as a function of the insufficiency;

training a machine learning model to predict compatible alimentary elements as a function of the filtered training data subset; and generating the compatible alimentary element to address the insufficiency as a function of the machine learning model; and displaying, by the at least a computing device, the compatible alimentary element from the alimentary instruction set using the graphical user interface.

11. The method of claim 10, wherein at least one preceding alimentary element of the plurality of preceding alimentary elements comprises a past alimentary element selected by the user from a plurality of compatible alimentary elements.

12. The method of claim 11, wherein at least a compatible alimentary element of the plurality of compatible alimentary elements comprises an alimentary element intended to address a nutrition deficiency.

13. The method of claim 10, wherein receiving the plurality of preceding alimentary elements further comprises receiving a plurality of timestamps, wherein the plurality of timestamps includes a timestamp associated with each preceding alimentary element of the plurality of alimentary elements.

14. The method of claim 10, wherein generating the adherence score further comprises determining the adherence score as a function of an accuracy parameter.

15. The method of claim 10, wherein identifying the insufficiency of an alimentary element comprises utilizing a insufficiency classifier to output an insufficient alimentary element.

16. The method of claim 10, wherein the insufficiency relates to non-selected compatible elements part of the alimentary element program.

17. The method of claim 10, wherein the insufficiency of the insufficient alimentary element relates a low accuracy parameter matched to the alimentary element.

18. The method of claim 10, wherein the alimentary instruction set comprises a supplement for a non-selected alimentary element.

* * * * *